(12) United States Patent
Griffin et al.

(10) Patent No.: US 11,622,860 B2
(45) Date of Patent: Apr. 11, 2023

(54) DEVICE FOR PERCUTANEOUS VENOUS VALVE REPAIR AND RELATED METHOD

(71) Applicants: Joseph Martin Griffin, Baton Rouge, LA (US); Paul Quentin Escudero, Redwood City, CA (US)

(72) Inventors: Joseph Martin Griffin, Baton Rouge, LA (US); Paul Quentin Escudero, Redwood City, CA (US)

( * ) Notice: Subject to any disclaimer, the term of this patent is extended or adjusted under 35 U.S.C. 154(b) by 190 days.

(21) Appl. No.: 17/173,899

(22) Filed: Feb. 11, 2021

(65) Prior Publication Data

US 2021/0161669 A1 Jun. 3, 2021

Related U.S. Application Data

(63) Continuation of application No. 16/591,682, filed on Oct. 3, 2019, now Pat. No. 10,959,849.

(60) Provisional application No. 62/771,199, filed on Nov. 26, 2018.

(51) Int. Cl.
*A61F 2/24* (2006.01)
*A61B 17/00* (2006.01)

(52) U.S. Cl.
CPC ...... *A61F 2/2466* (2013.01); *A61B 17/00234* (2013.01); *A61B 2017/00243* (2013.01); *A61B 2017/00292* (2013.01); *A61F 2/2475* (2013.01)

(58) Field of Classification Search
CPC ................ A61F 2/2466; A61F 2/2475; A61B 17/00234; A61B 17/122; A61B 17/1285; A61B 17/0682; A61B 17/0487; A61B 17/08; A61B 17/0401; A61B 17/128; A61B 2017/00243; A61B 2017/00292; A61B 2017/0488; A61B 2017/0409; A61B 2018/00702
See application file for complete search history.

(56) References Cited

U.S. PATENT DOCUMENTS

| | | | |
|---|---|---|---|
| 6,626,916 B1 * | 9/2003 | Yeung | A61B 17/0401 606/151 |
| 6,752,813 B2 | 6/2004 | Goldfarb et al. | |
| 7,815,661 B2 | 10/2010 | Mirizzi et al. | |
| 8,784,439 B1 | 7/2014 | Ward et al. | |

(Continued)

FOREIGN PATENT DOCUMENTS

WO 9117789 A1 11/1991

OTHER PUBLICATIONS

Author Unknown; "Percutaneous Valve Repair Procedure—You Tube"; TGWHFoundation; Published Feb. 9, 2009; 3 pages, last accessed on Sep. 6, 2019 at https://www.youtube.com/watch?v=N5Priyxj88k.
Jan de Borst, Gert et al.; "Percutaneous Venous Valve Designs for Treatment of Deep Venous Insufficiency"; Department of Vascular Surgery, University Medical Center Utrecht, The Netherlands.; J. Endovasc Ther; 2012; 19; pp. 291-302.
Zervides, Constantinos et al.; "Historical Overview of Venous Valve Prostheses for the Treatment of Deep Venous Valve Insufficiency"; J. Endovasc Ther; 2012; 19; pp. 281-290.

(Continued)

*Primary Examiner* — Erich G Herbermann
(74) *Attorney, Agent, or Firm* — Phelps Dunbar, LLP; R. Andrew Patty, II

(57) ABSTRACT

A device for percutaneous venous valve repair generally including a catheter and a retractable and extendable member for deploying an object that affixes a portion of a venous valve leaflet to an adjacent vein wall. A related method for percutaneous venous valve repair is revealed to include percutaneously inserting a device as described herein into a peripheral vasculature of a living subject so as to affix at least a portion of a leaflet of a venous valve to an adjacent vein wall.

14 Claims, 4 Drawing Sheets

(56) References Cited

U.S. PATENT DOCUMENTS

| | | | |
|---|---|---|---|
| 8,900,250 B2 * | 12/2014 | Fritscher-Ravens | A61B 10/04 606/110 |
| 8,900,253 B2 * | 12/2014 | Aranyi | A61B 17/122 606/142 |
| 9,925,074 B2 | 3/2018 | Hyodoh et al. | |
| 2005/0004575 A1 * | 1/2005 | Sgro | A61B 17/064 606/220 |
| 2005/0216039 A1 | 9/2005 | Lederman | |
| 2006/0282159 A1 | 12/2006 | Taheri | |
| 2015/0305801 A1 * | 10/2015 | Trieu | A61B 18/1477 606/41 |
| 2016/0045219 A1 * | 2/2016 | Guala | A61B 17/22 606/185 |

OTHER PUBLICATIONS

Cools, Bjorn et al.; "Transventricular Balloon Dilation and Stenting of the RVOT in Small Infants with Tetralogy of Fallot with Pulmonary Atresia"; Catheterization and Cardiovascular Interventions; 2012; 7 pages.

Migliara, Bruno et al.; "A Novel Technique to Create an Arteriovenous Fistula During Total Percutaneous Deep Foot Venous Arterialisation Using an IVUS Guided Catheter"; European Journal of Vascular Endovascular Surgery; May 2018; vol. 55; Issue 5; p. 735; 4 pages.

Shi, Hong-Jian et al.; "Percutaneous Mechanical Thrombectomy Combined with Catheter-Directed Thrombolysis in the Treatment of Symptomatic Lower Extremity Deep Venous Thrombosis"; European Journal of Radiology; Aug. 2009; vol. 71; Issue 2; pp. 350-355; 2 pages.

* cited by examiner

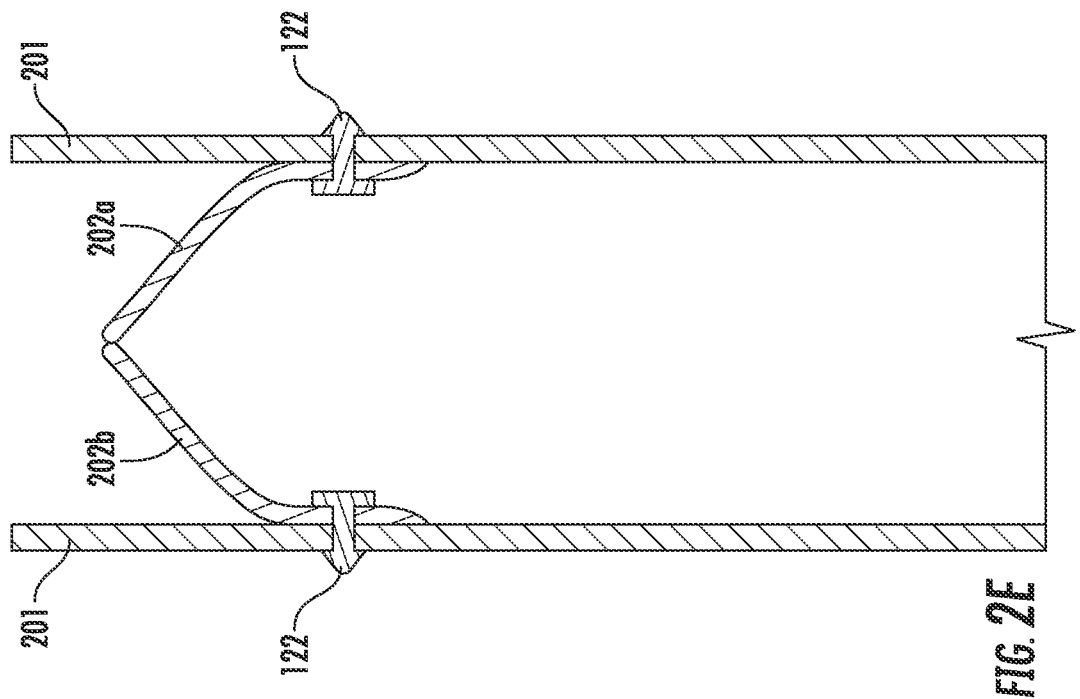
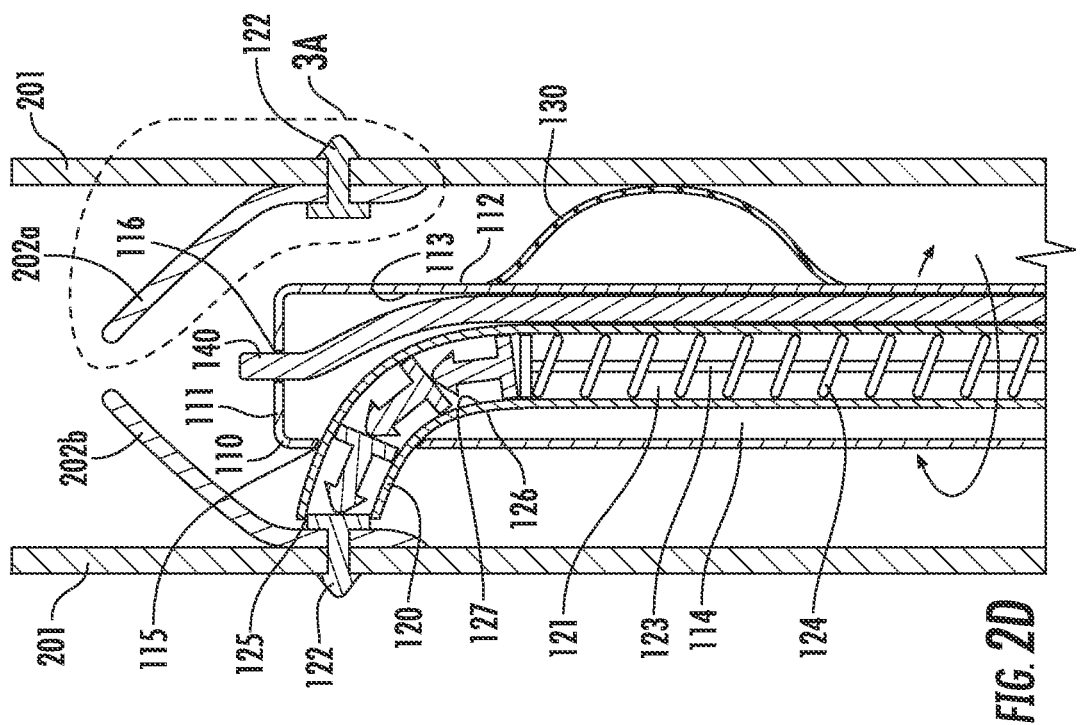
FIG. 2D
FIG. 2E

DEVICE FOR PERCUTANEOUS VENOUS VALVE REPAIR AND RELATED METHOD

CROSS-REFERENCE TO RELATED APPLICATIONS

This application is a continuation of U.S. application Ser. No. 16/591,682, filed Oct. 3, 2019, which claims the benefit of US Provisional Application No. 62/771,199, filed Nov. 26, 2018. Each patent application identified above is incorporated herein by reference in its entirety to provide continuity of disclosure.

STATEMENT REGARDING FEDERALLY SPONSORED RESEARCH OR DEVELOPMENT

Not applicable.

FIELD

The present disclosure generally relates to methods and devices for venous valve repair. More specifically, the present disclosure relates to methods and devices for percutaneous venous valve repair in a living subject.

BACKGROUND

This section introduces information that may be related to or provide context for some aspects of the subject matter described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Approximately 1% of the total human population and 3% to 5% of the population over the age of 65 will suffer from a venous leg ulcer (VLU). VLUs are often recurrent, can persist for years, and can result in infection, cellulitis, osteomyelitis, and/or amputation. In the United States, the financial burden of VLUs is estimated to be $2 billion annually and is expected to grow as the total population ages.

One of the major causes of ulcer formation is venous reflux/insufficiency. In spite of the development of some procedures able to treat superficial venous dysfunction in the lower limbs, advanced chronic venous insufficiency remains a burden. Many patients have to wear compression stockings, but poor patient compliance to this treatment suggests it is not a total solution with respect to the patient's expectations.

Blood return from the legs of a person occurs mainly through the deep veins. Within such veins are multiple venous valves, which are bicuspid (two) flap-like structures made of elastic tissue. The flap-like structures are often referred to as leaflets. The function of the valves is to keep blood moving in one direction.

A healthy leg has veins with smooth, elastic walls that are designed to adapt to the changes in pressure within a vein, which keeps blood moving in one direction: toward the heart. As the heart provides positive blood pressure to the arteries, the venous valves open to allow (return flow) one-way flow in the direction of the heart. When the positive pressure of the heartbeat subsides, the valves close to stop any back-flow.

However, if the walls of a vein have been damaged (e.g., by trauma, thrombosis, and so forth), then the valves may fail to close properly. When valves fail to close properly, blood can flow backward within the vein. This may result in blood pooling, putting pressure on lower leg veins, which may cause even more valves to fail over time. Thus, when the body is upright under these circumstances, the blood being transported back to the heart may stagnate in the legs. The pressure in the superficial veins directly under the skin may increase and cause the veins to become swollen. Tired, aching legs are the most common early symptoms of this condition—particularly after prolonged standing. Later, fluid may collect in the feet and ankles causing them to swell. The skin above the ankles may become thin and discolored or even breakdown to form a venous stasis ulcer. Venous disorders caused by improper closure of valves may range from varicose veins to deep vein thrombosis and post thrombotic syndrome.

Thus, a need exists for devices and methods to repair venous valves of a living subject.

SUMMARY

In general, the present disclosure provides a device and related method for percutaneous venous valve repair.

In an embodiment, the device includes a catheter and a retractable and extendable member. The catheter includes (i) a body having a proximal end and a distal end, (ii) at least one lumen, defined by the body of the catheter, that extends between the proximal end and the distal end of the catheter, (iii) at least one side port, defined by the distal end portion of the body of the catheter, wherein the at least one side port has an angle in the range of greater than about 0 degrees and less than about 90 degrees, the angle formed between a transverse axis of the catheter that is orthogonal to a central longitudinal axis of the catheter, and a central axis of the at least one side port, wherein all of the axes share a common intersection point, and (iv) at least one expandable member. The retractable and extendable member includes (i) a body having a proximal end and a distal end, (ii) a conduit, defined by the body of the retractable and extendable member, that extends between the proximal end and the distal end of the retractable and extendable member, (iii) at least one anchor positioned within the conduit, and (iv) an anchor deployment mechanism positioned within the conduit so as to cause the deployment of the at least one anchor through the conduit and the at least one side port of the catheter when the anchor deployment mechanism is activated. The retractable and extendable member is sized and configured to slide through the at least one lumen of the catheter and extend through the at least one side port of the catheter.

One or more aspects include the device of the preceding paragraph in which the expandable member comprises an inflatable balloon.

One or more aspects include the device of any preceding paragraph in which the retractable and extendable member further comprises one or more markers for identifying a location of the retractable and extendable member using external imaging, internal imaging, or both.

One or more aspects include the device of any preceding paragraph in which the catheter is sized and configured to allow an imaging device to slide through the at least one lumen of the catheter.

One or more aspects include the device of any preceding paragraph in which the anchor deployment mechanism is a spring-loaded mechanism.

One or more aspects include the device of any preceding paragraph in which the anchor deployment mechanism is a screw driven mechanism.

One or more aspects include the device of any preceding paragraph in which the catheter is rotatable.

One or more aspects include the device of any preceding paragraph in which the at least one anchor is bio-absorbable is a rivet, hook, or both.

One or more aspects include the device of any preceding paragraph in which the at least one side port has an angle in the range of about 10 degrees to about 45 degrees.

One or more aspects include the device of any preceding paragraph in which the at least one side port has an angle in the range of about 15 degrees to about 45 degrees.

In another aspect, the present disclosure provides a method for venous valve repair. The method includes (A) percutaneously inserting the device of any preceding paragraph into a peripheral vasculature of a subject, (B) traversing the distal end of the catheter through the peripheral vasculature of the subject to position the distal end of the catheter adjacent a venous valve of a vein of a subject, (C) traversing the retractable and extendable member through the lumen of the catheter, (D) positioning the distal end of the retractable and extendable member in sufficient proximity to a first leaflet of the venous valve of the vein of the subject so as to permit deployment of the at least one anchor to at least a portion of a first leaflet of the venous valve, and (E) applying the at least one anchor to the portion of the first leaflet of the venous valve so as to anchor at least a portion of the first leaflet to the vein of the subject.

One or more aspects include the method of the preceding paragraph in which in step (B) the distal end of the catheter is held in position by activating a pressure source or deflection system to expand an expandable member so as to cause the expandable member to contact a portion of a wall of the vein of the subject.

One or more aspects include the method of any preceding paragraph further comprising (F) abating or deflating the expandable member.

One or more aspects include the method of the preceding paragraph further comprising (G) rotating the catheter so as to position the distal end of the retractable and extendable member in sufficient proximity to the venous valve of the vein of the subject so as to permit deployment of the at least one anchor to at least a portion of a second leaflet of the venous valve; and (H) applying the at least one anchor to the portion of the second leaflet of the venous valve so as to anchor at least a portion of the second leaflet to the vein of the subject.

One or more aspects include the method of any preceding paragraph in which in step (B) the distal end of the catheter is positioned using an imaging system.

One or more aspects include the method of any preceding paragraph in which in step (D) the distal end of the retractable and extendable member is positioned by using a marker on the retractable and extendable member to identify a location of the retractable and extendable member relative to the vein of the subject using external imaging.

One or more aspects include the method of any preceding paragraph in which in step (E) the at least one anchor is applied to the portion of the first leaflet of the venous valve by activating the anchor deployment mechanism.

One or more aspects include the method of any preceding paragraph in which in step (B) the distal end of the catheter is positioned using an intravascular imaging system.

In another embodiment, the device includes a catheter and a retractable and extendable member. The catheter includes (i) a body having a proximal end and a distal end; (ii) a lumen, defined by the body of the catheter, that extends between the proximal end and the distal end of the catheter; (iii) at least one side port, defined by the distal end portion of the body of the catheter; and (iv) an expandable member. The retractable and extendable member includes (i) a body having a proximal end and a distal end; (ii) a conduit, defined by the body of the retractable and extendable member, that extends between the proximal end and the distal end of the retractable and extendable member; (iii) at least one anchor positioned within the conduit; and (iv) an anchor deployment mechanism positioned within the conduit so as to cause the deployment of the at least one anchor through the conduit and the at least one side port of the catheter when the anchor deployment mechanism is activated. The retractable and extendable member is sized and configured to slide through the lumen of the catheter and extend through the at least one side port of the catheter. Further, when the retractable and extendable member is in the extended position, an angle in the range of greater than about 0 degrees and less than about 90 degrees is formed between (i) a transverse axis of the catheter that is orthogonal to a central longitudinal axis of the catheter, and (ii) a central axis of the angled portion of the retractable and extendable member.

One or more aspects include the device of the preceding paragraph in which the angle is in the range of about 10 degrees to about 45 degrees.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE DRAWINGS

The claimed subject matter may be understood by reference to the following description taken in conjunction with the accompanying drawings, in which like reference numerals identify like elements, and in which:

FIG. 2D illustrates the device of FIG. 1 applying at least one anchor to a portion of a leaflet of a venous valve so as to anchor at least a portion of the leaflet to the vein.

FIG. 2E illustrates a cross-sectional view of a vein having each of the valve leaflets repaired by the device of FIG. 2, in which the valve is closing properly.

Figure 1:
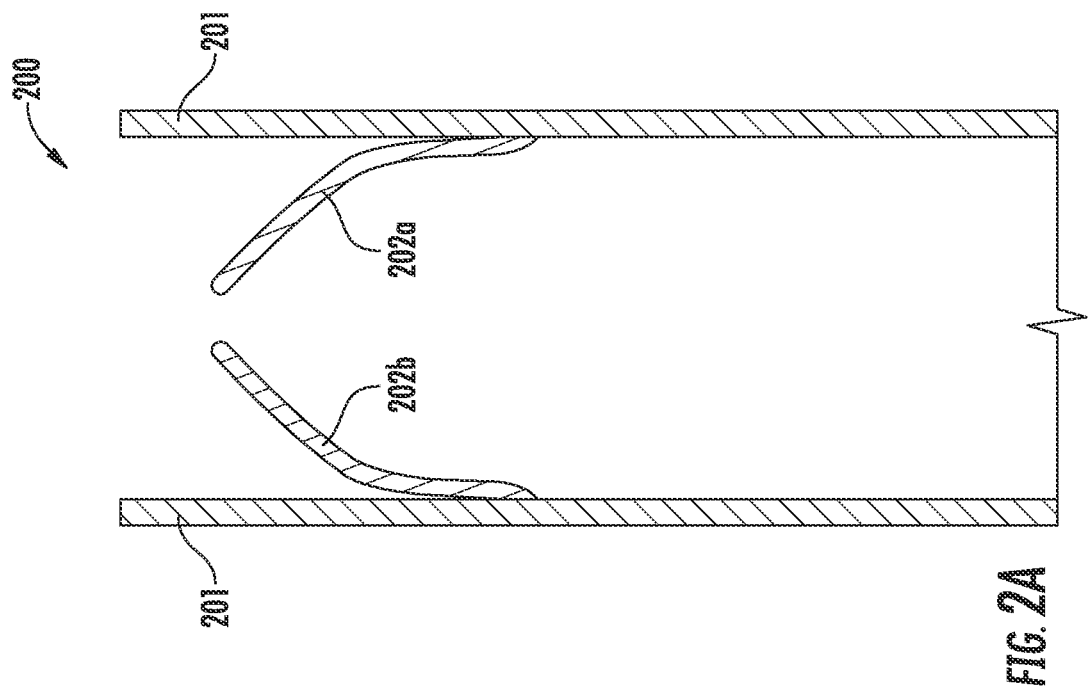
FIG. 1 illustrates a cross-sectional view of a device for percutaneous venous valve repair according to one or more aspects of the present disclosure.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

Definitions

To define more clearly the terms used in this disclosure, the following definitions are provided. Unless otherwise indicated, the following definitions are applicable to this disclosure. To the extent that any definition or usage provided by any document incorporated here by reference conflicts with the definition or usage provided herein, the definition or usage provided in this disclosure controls.

In this disclosure, features of the subject matter are described such that, within particular aspects, a combination of different features can be envisioned. For each and every aspect and each and every feature disclosed herein, all combinations that do not detrimentally affect the devices, systems, processes, or methods described herein are contemplated with or without explicit description of the particular combination. Additionally, unless explicitly recited otherwise, any aspect or feature disclosed herein can be combined to describe inventive devices, systems, processes, or methods consistent with the present disclosure.

In this disclosure, while devices and methods are often described in terms of "comprising" various components or steps, the devices and methods can also "consist essentially of" or "consist of" the various components or steps, unless stated otherwise. For example, a device for venous valve repair consistent with aspects of the disclosed subject matter can comprise; alternatively, can consist essentially of; or alternatively, can consist of the various component, unless stated otherwise. Similarly, a method for venous valve repair consistent with aspects of the disclosed subject matter can comprise; alternatively, can consist essentially of, or alternatively, can consist of the various steps, unless stated otherwise. For example a device for percutaneous venous valve repair consistent with aspects of the disclosed subject matter can comprise; alternatively, can consist essentially of; or alternatively, can consist of, the indicated components thereof.

The terms "a," "an," and "the" are intended to include plural alternatives, e.g., at least one, one or more, and one or more than one, unless otherwise specified.

Although any methods and materials similar or equivalent to those described herein can be used in the practice or testing of the subject matter described herein, the typical methods and materials are herein described.

All publications and patents mentioned herein are incorporated herein by reference for the purpose of describing and disclosing, for example, the constructs and methodologies that are described in the publications, which can be used in connection with the presently described subject matter.

Various numerical ranges are disclosed herein. When a range of any type is disclosed or claimed herein (e.g., "ranging from . . . ", "in a range of from . . . ", "in the range of from . . . ") the intent is to disclose or claim individually each possible number that such a range could reasonably encompass, including end points of the range as well as any sub-ranges and combinations of sub-ranges encompassed therein, unless otherwise specified. For example, the present application discloses that the at least one side port, in certain aspects, can have an angle in the range of about 10 degrees to about 45 degrees. By a disclosure that the at least one side-port has an angle in a range or ranging from about 10 degrees to about 45 degrees, the intent is to recite that the angle of the at least one side port can be any angle within the range and, for example, can be equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 degrees. Additionally, the angle of the at least one side-port can be within any range from 10 to 45 degrees (for example, the angle of the at least one side-port can be in a range 15 to 40 degrees), and this also includes any combination of ranges between 10 and 45 degrees. Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. Whether or not modified by the term "about," the claims include equivalents to the specified quantities.

DETAILED DESCRIPTION

Illustrative aspects of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

I. Devices for Venous Valve Repair

Aspects of the disclosed subject matter are directed to devices for percutaneously repairing a venous valve. FIG. 1 illustrates a device 100 for percutaneous venous valve repair that comprises a catheter 110, and a retractable and extendable member 120.

A. Catheter

The catheter 100 comprises (i) a body having a proximal end (not shown) and a distal end 111, (ii) at least one lumen 114, (iii) at least one side port 115, and (iv) at least one expandable member 130.

A1. Body of the Catheter

The device 100 is sized and configured for introduction into any appropriate percutaneous pathway of a subject for venous valve repair, for example, into a popliteal vein of a subject, femoral vein, and so forth. The body of the catheter is a flexible, elongated member, having at least one outer side wall 112 and at least one inner side wall 113. The body of the catheter may be rotated in multiple orientations, for example, the body of the catheter may be rotated in the range of greater than 0 degrees to less than 360 degrees so as to orient the device in a desired manner within the vein of a subject.

Lumen 114 is defined by the body of catheter 100 and extends between the proximal end and the distal end 111 of catheter 110. In an aspect, lumen 114 may be multi-member compatible. For example, lumen 114 of catheter 110 can be sized and configured to hold one or more additional members and allow the one or more additional members to slide through lumen 114 of catheter 100. Examples of suitable additional members include, without limitation, a member selected from the group consisting of a retractable and extendable member, an imaging system, a guide wire, and any combination of two or more of the foregoing.

In a further aspect, lumen 114 may be subdivided into multiple separate lumens, each of which is capable of holding one or more members. For example, lumen 114 may be subdivided into three separate lumens with each separate lumen sized and configured to hold one or more members such as a retractable and extendable member, an imaging system, a guide wire, or any combination of two or more of the foregoing.

The dimensions of catheter 110 may depend on many factors including, without limitation, the physical characteristics and health of the subject treated and the methods and/or approaches used for venous valve repair in the subject. For example the body of the catheter 110 may be any shape which in cross-section are round, oval, or elliptical, for example, the body of the catheter may have a generally tubular or cylindrical shape. The catheter may have length in the range of about 60 to about 130 centimeters, or a length in range of about 50 to about 110 centimeters. In another aspect, catheter 110 may have a diameter in the range of about 2.3 to about 3.6 millimeters, or a diameter in the range of about 2.6 to about 4.0 millimeters in diameter. As an example, a catheter 110 having a length in the range of about 60 to about 130 centimeters in length with a diameter of about 3 millimeters can be introduced into peripheral vasculature of a subject and guided through a percutaneous pathway of a subject for venous valve repair by a popliteal vein approach. The side wall of the body of catheter 100 may have a thickness in the range of about 0.13 to about 0.8 millimeters, as measured from the outer surface of inner side wall 113 of the body of catheter 110 to the outer surface of outer side wall 112 of the body of catheter 110.

The body of catheter 110 may be made of any suitable material or combination of materials that provide both the strength and flexibility suitable to resist collapse by external forces, such as forces imposed during rotations, bending and/or twisting. Suitable examples of materials that may be used include, without limitation polyethylene, polyurethane, nylon, stainless steel, or any combination of two or more of the foregoing.

In further aspects, at least a portion of outer side wall 112 of the body of catheter 110 may be coated with a substance that aids with the insertion of catheter 110 into the vasculature of a subject and/or aids in the movement of catheter 100 through the vasculature of a subject during percutaneous venous valve repair. Suitable examples of substances that may be used include, without limitation Image result for polytetrafluoroethylene (PTFE) jacket or hydrophilic coating, or any combination of two or more of the foregoing.

In still further aspects, the body of catheter 110 may define one or more apertures 116 configured to permit use of an imaging system with the device 100. For example, as illustrated in FIG. 1, the body of catheter 100 may have one or more apertures 116 located at its distal end 111 to permit an imaging device or system 140 to have a field of view external to catheter 110. The dimensions of apertures 116 may depend on many factors including, without limitation, the structure of the imaging device or system 140. For example, the one or apertures 116 may have a diameter in the range of about 1.4 to about 2.8 millimeters.

A2. At Least One Side Port of the Catheter

Side port 115 of catheter 100 is defined by the distal end portion of the body of catheter 110. In an aspect, side port 115 of catheter 100 is located at a distance in the range of about 5 to about 30 millimeters from the distal end 111 of catheter 100, as measured along the length of a central longitudinal axis of catheter 100, such axis being designated as $L_1$ in FIG. 1.

Side port 115 has an angle α that is defined as the angle formed between (i) a transverse axis of the catheter, $L_2$, that is orthogonal to the central longitudinal axis of the catheter, $L_1$, and (ii) a central axis of the at least one side port, $L_3$. Each of the above mentioned axes (i.e., $L_1$, $L_2$, and $L_3$) share a common intersection point, P1.

In an aspect, side port 115 has an angle α which is greater than 0 degrees and less than 90 degrees. In another aspect, the at least one side port 115 has an angle α in the range of about 10 to about 45 degrees, and more preferably an angle α in the range of about 15 to about 45 degrees. Providing such an angle α for side port 115 permits positioning of retractable and extendable member 120 in a suitable location to allow device 100 to apply at least one anchor 122 to a portion of a leaflet 202a, 202b of a venous valve of a subject so as to anchor at least a portion of the leaflet 202a, 202b to a portion of vein wall 201 of the subject.

In another aspect, angle α of side port 115 may be defined as the angle formed between the transverse axis of the catheter $L_2$ that is orthogonal to the central longitudinal axis of catheter $L_1$, and a central axis of the angled portion of the retractable and extendable member, $L_3$, when retractable and extendable member 120 is in the extended position, for example, extended through side port 115 of catheter 110.

The dimensions of side port 115 can depend on many factors including, without limitation, the structure of the retractable and extendable member 120. In an aspect, side port 115 has a diameter in the range of about 0.5 to about 1.5 millimeters, or about 1 to about 2.5 millimeters.

In another aspect, catheter 110 can include multiple side ports, each defined by the distal end portion of the body of catheter 110. For example, catheter 110 can have at least two side ports: a first side port and a second side port, each side port defined on a respective side of the catheter (e.g., first side port positioned 180 degrees from the second side port) to facilitate simultaneous deployment of anchors or staged deployment to repair the venous valve.

A3. At Least One Expandable Member

Catheter 110 may further comprise at least one expandable member 130 configured to expand a vein 200 of a subject in a location adjacent a valve leaflet 202a, 202b of a subject so as to dilate vein 200 during venous valve repair and maintain device 100 in a desired location within vein 200. Expandable member 130 may be carried or positioned on the outer surface of the body of catheter 110, for example, disposed on the outer surface of a distal end portion of catheter 110. Expandable member 130 may expand and/or contract in vein 200 upon activation by an operator.

Suitable examples of expandable members 130 include, without limitation, inflatable balloons, shaped deflection systems (e.g., wire mesh structures), electrically or temperature activated nitinol expandable members, or polymer based expandable members.

In an aspect, expandable member 130 may be configured to deliver a substance to vein 200 so as to cause a desire therapeutic response from vein 200. For example, the outer surface of expandable member 130 may be coated with a bioactive substance that delays the healing response at or near the location of the venous valve repair.

Suitable examples of bioactive substances include, without limitation, examples are serilimus or palitaxel, each of which are commercially available from Pfizer Inc. or Phyton Biotech, LLC.

B. Retractable and Extendable Member

Retractable and extendable member 120 comprises (i) a body having a proximal end (not shown) and a distal end 125, (ii) a conduit 121, (iii) at least one anchor 122 positioned within conduit 121, and (iv) an anchor deployment mechanism 123 positioned within conduit 121.

B1. Body of the Retractable and Extendable Member

Retractable and extendable member 120 comprises a body having a proximal end and a distal end 125. Retractable and extendable member 120 is a flexible, elongated member, having at least one outer side wall 126 and at least one inner side wall 127. Retractable and extendable member 120 is sized and configured to slide through lumen 114 of catheter 110 and extend through side port 125 of catheter 110. Further, retractable and extendable member 120 can both extend and retract through side port 125 of catheter 110. Retractable and extendable member 120 may be actuated (e.g., extended and/or retracted) via an actuating device, such as a thumb slider operatively connected to retractable and extendable member 120.

Conduit 121 of retractable and extendable member 120 is defined by the body of retractable and extendable member 120. Conduit 121 of retractable and extendable member 120 extends between the proximal end and distal end 125 of retractable and extendable member 120, and permits anchor deployment mechanism 123 to slide within conduit 114, and allow application anchor deployment mechanism 123 to apply at least one anchor 122 to a portion of a leaflet 202a, 202b of a venous valve of a subject so as to anchor at least a portion of leaflet 202a, 202b to vein 200 of the subject.

The dimensions of retractable and extendable member 120 may depend on many factors including, without limitation, the physical characteristics and structure of catheter 110. Thus, in an aspect, the body of retractable and extendable member 120 may be any shape which in cross-section is round, oval, or elliptical, for example, and the body of catheter 110 may have a generally tubular or cylindrical shape.

Retractable and extendable member 120 may have a length in the range of about 0.2 to 1.5 about centimeters, or a length in range of about 0.1 to about 2.0 centimeters. In another aspect, retractable and extendable member 120 has a diameter in the range of about 0.5 to 1.5 about millimeters, or a diameter in the range of about 1.0 to about 2.5 millimeters in diameter. For example, if used with a catheter 110 having a length in the range of about 60 to 130 about centimeters in length with a diameter of about 3 millimeters, retractable and extendable member 120 may have a length in the range of about 0.2 to about 1.5 centimeters in length with a diameter of about 3 millimeters. The side wall of the body of retractable and extendable member 120 has a thickness in the range of about 0.13 to about 0.8 millimeters, as measured from the outer surface of inner side wall 127 of retractable and extendable member 120 to the outer surface of outer side wall 126 of retractable and extendable member 120.

The body of retractable and extendable member 120 may be made of any suitable material or combination of materials that provide both the strength and flexibility suitable to resist collapse by external forces, such as forces imposed during bending or twisting. Suitable examples of materials that may be used include, without limitation, polyethylene, polyurethane, nylon, stainless steel, or any combination of two or more of the foregoing.

In a further aspect, the body of retractable and extendable member 120 of device 100 may comprise one or more markers 124, disposed thereon (e.g., on outer surface of retractable and extendable member 120) for identifying a location of retractable and extendable member 120 during a venous valve repair procedure, for example, by using markers 124 with external imaging, internal imaging, or both. Suitable examples of such marker(s) include radioopaque markers or receiver coils to enhance visualization by fluoroscopy, MRI or X-ray, or etched grooves to enhance visualization by ultrasound imaging, including echocardiography.

B2. At Least One Anchor

Retractable and extendable member 120 comprises at least one anchor 122 positioned within conduit 121. Anchor 122 is configured to tack and adhere at least a portion of a leaflet 202a, 202b of a venous valve to wall 201 of vein 200. In other aspects, retractable and extendable member 120 may comprise more than one anchor 122, for example, as shown in FIG. 1 and FIGS. 2A-2E. As illustrated in FIGS. 3A-3B, anchor 122 may be in the form of a rivet, hook, or both. In another aspect, as shown in FIG. 3C, anchor 122 may be in the form of a suture.

In an aspect, each anchor 122 comprises a bio-absorbable material that can be absorbed by the subject once the area at or near the venous valve repair location has healed. By using such a material, anchor 122 does not have to remain in place permanently at or near the area of the venous valve repair. Suitable examples of materials for constituting anchor 122 include, without limitation, polyglycolic acid or polylactic acid, each of which are commercially available from Teleflex Incorporated.

B3. Anchor Deployment Mechanism

Retractable and extendable member 120 further comprise an anchor deployment mechanism 123. Anchor deployment mechanism 123 is positioned within conduit 121 and configured to slide within conduit 121 so as to cause the deployment of anchor 122 through the conduit 121 and respective side port 125 of catheter 110 when anchor deployment mechanism 123 is activated. In an aspect, anchor deployment mechanism 123 may comprise a shaft coupled to a seat, for example, in the form of a plunger structure.

In an aspect, anchor deployment mechanism 123 is a spring-loaded mechanism, which under the control of an operator deploys anchor 122 upon activation.

In another aspect, anchor deployment mechanism 123 is a screw driven mechanism, which under the control of an operator deploys anchor 122 upon activation.

C. Additional Component(s) of Device

C1. Imaging System

In an aspect, device 100 may further comprise an imaging system 140 to aid in the positioning of distal end 111 of catheter 110 and/or distal end 125 of retractable and extendable member 120 in sufficient proximity to leaflet 202a, 202b of the venous valve of the vein of the subject so as to permit deployment of anchor 122 to at least a portion of leaflet 202a, 202b of the venous valve.

In an aspect, imaging system 140 may be held in lumen 114 of catheter 110. Suitable examples of imaging system 140 include, without limitation, instravascular ultrasound (IVUS) or optical coherence tomography (OCT), such as Philips/Volcano IVUS, Boston Scientific IVUS, Avinger OCT.

C2. Guide Wire

In an aspect, device 100 may further comprise one or more guide wires to aid in placement of the device in the peripheral vasculature of a subject during a venous valve repair. The guide wires may be incorporated into lumen 114 of catheter 110, conduit 121 of extendable and retractable 120, or both.

If a guide wire is used in conjunction with catheter 110, the guide wire is sized and configure so as to operate with catheter 110, and may be longer than catheter 110. For example, a guide wire having a length of about 145 to about 300 centimeters and a diameter of about 0.014 to about 0.035 millimeters in can be used with catheter 110 described above.

Suitable examples of guide wires include, without limitation, Hi-Torque Supra Core, which is commercially available from Boston Scientific Corporation, Abbott Laboratories, Terumo Corporation.

C3. Mechanisms to Operate the Device

In a further aspect, device 100 can include a guide collar, handgrip, handle, and other structures or devices at its proximal end (not shown) that aid in operation of the device. A variety of control mechanisms (e.g., electrical, optical, and/or mechanical control mechanisms), may be attached to catheter 110 via a guide collar (not shown). For example, a guide wire can be included as a mechanical control mechanism. The guide collar can include additional operational features, such as a grip for aiding manual control of the catheter, markers indicating the orientation of the lumen of the catheter, markers to gauge the depth of catheter advancement, instruments to measure catheter operation or physiological signs of the subject (for example, a temperature gauge or pressure monitor), or an injector control mechanism coupled to the lumen of the catheter for delivering a small, precise volume of substances.

II. Methods for Venous Valve Repair

Figure 2A:
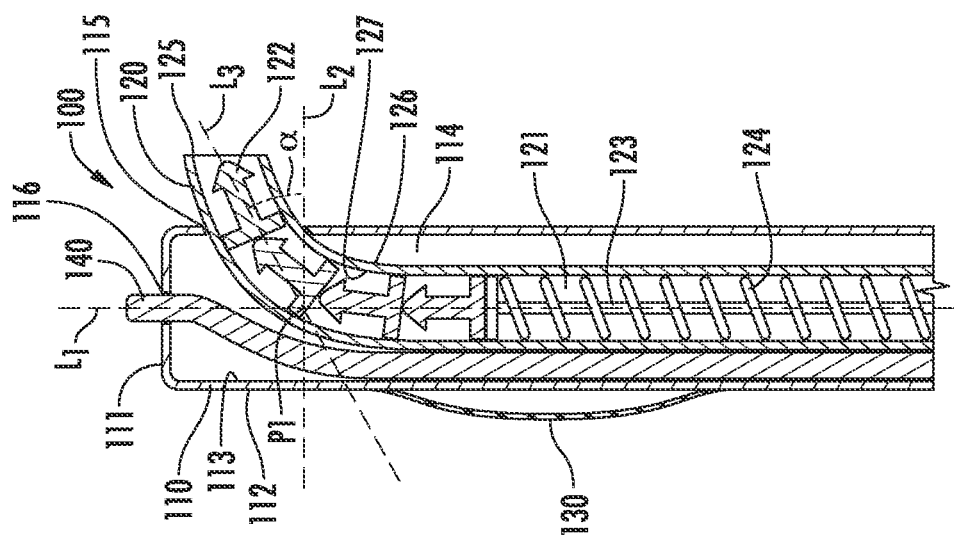
FIG. 2A illustrates a cross-sectional view of a venous valve, including valve leaflets, which is not closing properly.

Methods for using the above devices for venous valve repair are disclosed herein, and various steps of one such method is illustrated in FIGS. 2A-2E. FIG. 2A illustrates a cross-sectional view of a vein, including valve leaflets, which is not closing properly.

Figure 2B:
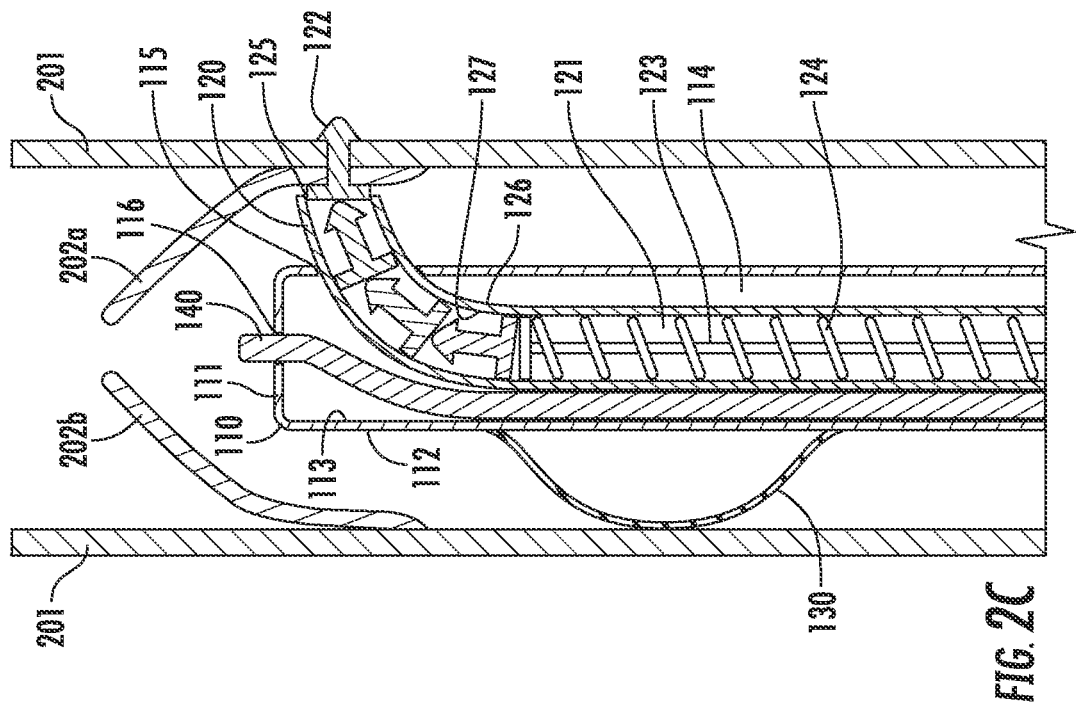
FIG. 2B illustrates the device of FIG. 1 positioned adjacent a leaflet of a venous valve shown in FIG. 2A.
Figure 2C:
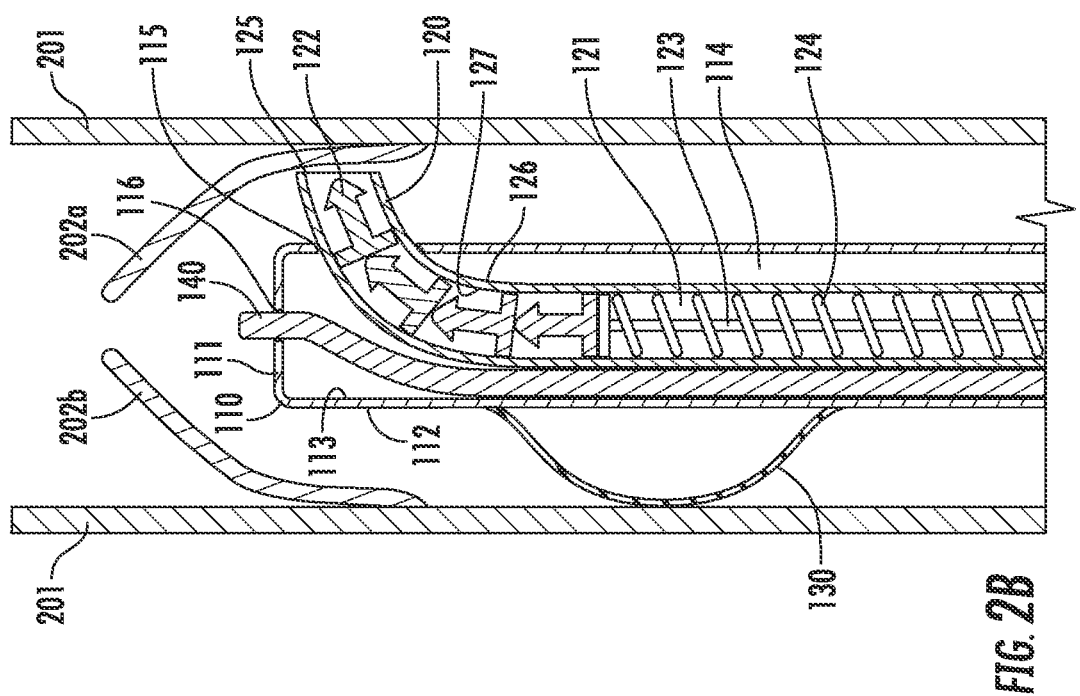
FIG. 2C illustrates the device of FIG. 1 applying at least one anchor to a portion of a leaflet of a venous valve so as to anchor at least a portion of the leaflet to the vein.
Figure 3A:
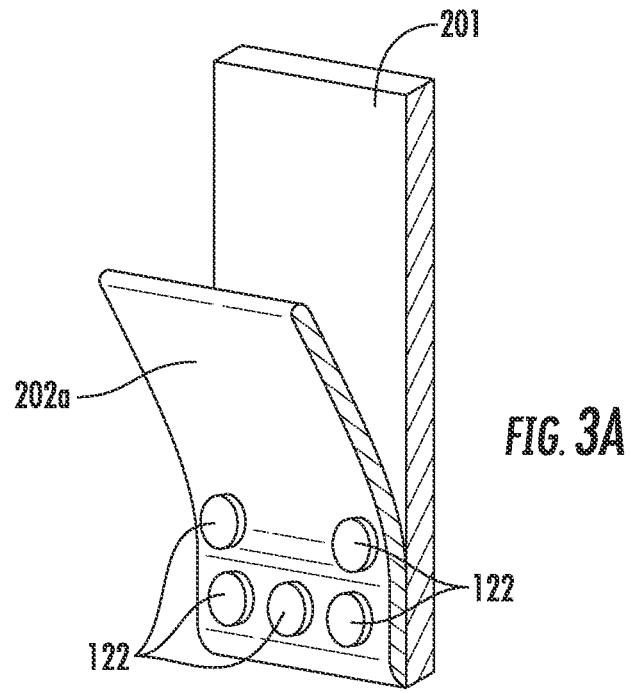
FIG. 3A illustrates one or more anchors applied a portion of a leaflet of a venous valve, where each of the one or more anchors are in the form of a rivet.
Figure 3B:
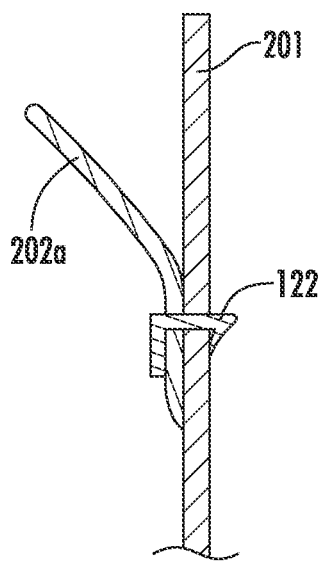
FIG. 3B illustrates one or more anchors applied a portion of a leaflet of a venous valve, where each of the one or more anchors are in the form of a hook.
Figure 3C:
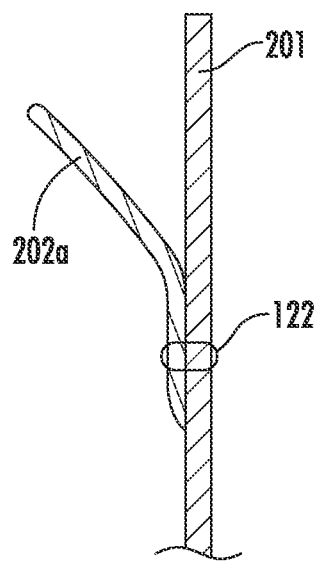
FIG. 3C illustrates one or more anchors applied a portion of a leaflet of a venous valve, where each of the one or more anchors are in the form of a suture.

In an aspect, a method for percutaneous venous valve repair comprises (A) percutaneously inserting one or more of devices 100 for venous valve repair described herein into a peripheral vasculature of a subject, (B) traversing distal end 111 of the catheter 110 through the peripheral vasculature of the subject to position distal end 111 of catheter 110 adjacent a venous valve of a vein 200 of a subject, (C) traversing the retractable and extendable member through lumen 114 of catheter 110, (D) positioning distal end 125 of retractable and extendable member 120 in sufficient proximity to a first leaflet 202a of the venous valve of vein 200 of the subject so as to permit deployment of anchor 122 to at least a portion of first leaflet 202a of the venous valve, as shown in FIG. 2B, and (E) applying anchor 122 to the portion of the first leaflet 202a of the venous valve so as to anchor at least a portion of the first leaflet 202a to the vein 200 of the subject, as shown in FIG. 2C. FIG. 2E shows a vein having each of the valve leaflets repaired by the device of FIG. 2, in which the valve is closing properly. Anchor 122 can be applied in any suitable direction as may be dictated by the particular characteristics and state of the venous valve, for example, anchor 122 may be horizontally and/or vertically applied to the leaflet of the venous valve as shown in FIG. 3A. In certain aspects, device 100 may be inserted into the popliteal vein for treating venous valve.

In an aspect, in step (B) of the method for percutaneous venous valve repair distal end 111 of catheter 110 may be held in position by activating a pressure source or deflection system to expand an expandable member 130 so as to cause expandable member 130 to contact a portion of wall 201 of vein 200 of the subject.

In an aspect, the method for percutaneous venous valve repair may further comprise delivering a substance to wall 201 of vein 200, for example, a substance that can cause a desired therapeutic response from the vessel. For example, at least a portion of the outer surface of expandable member 130 may be coated with a bioactive substance, which delays the healing response at or near the location of the venous valve repair, that is delivered when expandable member 130 is activated and contacts wall 201 of vein 200.

In an aspect, the method for percutaneous venous valve repair may further comprise (F) abating or deflating expandable member 130.

In an aspect, as illustrated in FIG. 2D, the method of for percutaneous venous valve repair can further comprise (G) rotating catheter 110 so as to position distal end 125 of retractable and extendable member 120 in sufficient proximity to the venous valve of vein 200 of the subject so as to permit deployment of at least one anchor 122 to at least a portion of a second leaflet 202b of the venous valve. As described above, the body of catheter 110 may be rotated within the vein by an amount of rotation which is greater than 0 degrees but less than 360 degrees.

In an aspect, the method for percutaneous venous valve repair may further comprise (H) applying at least one anchor 122 to the portion of second leaflet 202b of the venous valve so as to anchor the portion of second leaflet 202b to vein 200 of the subject, as illustrated in FIG. 2D.

In an aspect of the method for percutaneous venous valve repair distal end 111 of catheter 110 is positioned using an imaging system or device.

In an aspect, in step (D) of the method for percutaneous venous valve repair distal end 125 of retractable and extendable member 120 is positioned by using one or more markers 124 on retractable and extendable member 120 to identify a location of retractable and extendable member 120 relative to vein 200 of the subject using external imaging.

In an aspect of the method for percutaneous venous valve repair at least one anchor 122 is applied to the portion of the first or second leaflet 202a, 202b of the venous valve by activating the anchor deployment mechanism 123.

In an aspect of the method for percutaneous venous valve repair distal end 111 of catheter 110 is positioned using an imaging system, for example, an intravascular imaging system Volcano IVUS, Boston Scientific IVUS, or any combination of two or more of the foregoing.

The subject matter is described above with reference to numerous aspects and specific examples. Many variations will suggest themselves to those skilled in the art in light of the above detailed description. All such obvious variations are within the full intended scope of the appended claims. Other aspects of the subject matter disclosed herein can include, but are not limited to, the following (aspects are described as "comprising" but, alternatively, can "consist essentially of", or "consist of"):

Aspect 1. A device for percutaneous venous valve repair comprising:

(A) a catheter comprising: (i) a body having a proximal end and a distal end; (ii) at least one lumen, defined by the body of the catheter, that extends between the proximal end and the distal end of the catheter; (iii) at least one side port, defined by the distal end portion of the body of the catheter, wherein the at least one side port has an angle in the range of greater than about 0 degrees and less than about 90 degrees, the angle formed between a transverse axis of the catheter that is orthogonal to a central longitudinal axis of the catheter, and a central axis of the at least one side port, wherein all of the axes share a common intersection point; and (iv) at least one expandable member;

(B) a retractable and extendable member comprising: (i) a body having a proximal end and a distal end; (ii) a conduit, defined by the body of the retractable and extendable member, that extends between the proximal end and the distal end of the retractable and extendable member; (iii) at least one anchor positioned within the conduit; and (iv) an anchor deployment mechanism positioned within the conduit so as to cause the deployment of the at least one anchor through the conduit and the at least one side port of the catheter when the anchor deployment mechanism is activated;

wherein the retractable and extendable member is sized and configured to slide through the at least one lumen of the catheter and extend through the at least one side port of the catheter.

Aspect 2. The device as defined by Aspect 1, wherein the expandable member comprises an inflatable balloon.

Aspect 3. The device as defined by any of Aspects 1-2, wherein the retractable and extendable member further comprises one or more markers for identifying a location of the retractable and extendable member using external imaging, internal imaging, or both.

Aspect 4. The device as defined by any of Aspects 1-3, wherein the catheter is sized and configured to allow an imaging device to slide through the at least one lumen of the catheter.

Aspect 5. The device as defined by any of Aspects 1-4, wherein the anchor deployment mechanism is a spring-loaded mechanism.

Aspect 6. The device as defined by any of Aspects 1-5, wherein the anchor deployment mechanism is a screw driven mechanism.

Aspect 7. The device as defined by any of Aspects 1-6, wherein the catheter is rotatable.

Aspect 8. The device as defined by any of Aspects 1-7, wherein the at least one anchor is bio-absorbable is a rivet, hook, or both.

Aspect 9. The device as defined by any of Aspects 1-8, wherein the at least one side port has an angle in the range of about 10 degrees to about 45 degrees.

Aspect 10. The device as defined by any of Aspects 1-9, wherein the at least one side port has an angle in the range of about 15 degrees to about 45 degrees.

Aspect 11. A method for percutaneous venous valve repair comprising:

(A) percutaneously inserting the device as defined by any of Aspects 1-10 into a peripheral vasculature of a subject;

(B) traversing the distal end of the catheter through the peripheral vasculature of the subject to position the distal end of the catheter adjacent a venous valve of a vein of a subject;

(C) traversing the retractable and extendable member through the lumen of the catheter;

(D) positioning the distal end of the retractable and extendable member in sufficient proximity to a first leaflet of the venous valve of the vein of the subject so as to permit deployment of the at least one anchor to at least a portion of a first leaflet of the venous valve; and (E) applying the at least one anchor to the portion of the first leaflet of the venous valve so as to anchor at least a portion of the first leaflet to the vein of the subject.

Aspect 12. The method as defined by Aspect 11, wherein in step (B) the distal end of the catheter is held in position by activating a pressure source or deflection system to expand an expandable member so as to cause the expandable member to contact a portion of a wall of the vein of the subject.

Aspect 13. The method as defined by any of Aspects 11-12, further comprising (F) abating or deflating the expandable member.

Aspect 14. The method as defined by any of Aspects 11-13, further comprising (G) rotating the catheter so as to position the distal end of the retractable and extendable member in sufficient proximity to the venous valve of the vein of the subject so as to permit deployment of the at least one anchor to at least a portion of a second leaflet of the venous valve; and (H) applying the at least one anchor to the portion of the second leaflet of the venous valve so as to anchor at least a portion of the second leaflet to the vein of the subject.

Aspect 15. The method as defined by any of Aspects 11-14, wherein in step (B) the distal end of the catheter is positioned using an imaging system.

Aspect 16. The method as defined by any of Aspects 11-15, wherein in step (D) the distal end of the retractable and extendable member is positioned by using a marker on the retractable and extendable member to identify a location of the retractable and extendable member relative to the vein of the subject using external imaging.

Aspect 17. The method as defined by any of Aspects 11-16, wherein in step (E) the at least one anchor is applied to the portion of the first leaflet of the venous valve by activating the anchor deployment mechanism.

Aspect 18. The method as defined by any of Aspects 11-17, wherein in step (B) the distal end of the catheter is positioned using an intravascular imaging system.

Aspect 19. A device for venous valve repair comprising:

(A) a catheter comprising: (i) a body having a proximal end and a distal end; (ii) a lumen, defined by the body of the catheter, that extends between the proximal end and the distal end of the catheter; (iii) at least one side port, defined by the distal end portion of the body of the catheter; and (iv) an expandable member;

(B) a retractable and extendable member comprising: (i) a body having a proximal end and a distal end; (ii) a conduit, defined by the body of the retractable and extendable member, that extends between the proximal end and the distal end of the retractable and extendable member; (iii) at least one anchor positioned within the conduit; and (iv) an anchor deployment mechanism positioned within the conduit so as to cause the deployment of the at least one anchor through the conduit and the at least one side port of the catheter when the anchor deployment mechanism is activated;

wherein the retractable and extendable member is sized and configured to slide through the lumen of the catheter and extend through the at least one side port of the catheter;

wherein when the retractable and extendable member is in the extended position, an angle in the range of greater than about 0 degrees and less than about 90 degrees is formed between (i) a transverse axis of the catheter that is orthogonal to a central longitudinal axis of the catheter, and (ii) a central axis of the angled portion of the retractable and extendable member.

Aspect 20. The device as defined by Aspect 19, wherein the angle is in the range of about 10 degrees to about 45 degrees.

What is claimed is:

1. A device for percutaneous venous valve repair comprising: (A) a catheter comprising: (i) a body having a proximal end and a distal end; (ii) at least one lumen, defined by the body of the catheter, that extends between the proximal end and the distal end of the catheter; (iii) at least one side port, defined by a distal end portion of the body of the catheter, wherein the at least one side port has an angle in the range of greater than about 0 degrees and less than about 90 degrees, the angle being formed between a transverse axis of the catheter that is orthogonal to a central longitudinal axis of the catheter, and a central axis of the at least one side port, wherein all of the axes share a common intersection point; and (iv) at least one expandable member; (B) a retractable and extendable member comprising: (i) a body having a proximal end and a distal end; (ii) a conduit, defined by the body of the retractable and extendable member, that extends between the proximal end and the distal end of the retractable and extendable member; (iii) at least one anchor positioned within the conduit; and (iv) an anchor deployment mechanism positioned within the conduit so as to cause deployment of the at least one anchor through the conduit and the at least one side port of the catheter when the anchor deployment mechanism is activated; wherein the retractable and extendable member is sized and configured to bend and slide through the at least one lumen of the catheter and extend through the at least one side port of the catheter.

2. The device of claim 1 wherein the expandable member comprises an inflatable balloon.

3. The device of claim 1 wherein the retractable and extendable member further comprises one or more markers for identifying a location of the retractable and extendable member using external imaging, internal imaging, or both.

4. The device of claim 1 wherein the catheter is sized and configured to allow an imaging device to slide through the at least one lumen of the catheter.

5. The device of claim 1 wherein the anchor deployment mechanism is a spring-loaded mechanism.

6. The device of claim 1 wherein the anchor deployment mechanism is a screw driven mechanism.

7. The device of claim 1 wherein the catheter is rotatable.

8. The device of claim 1 wherein the at least one anchor is bio-absorbable and is a rivet, hook, or both.

9. The device of claim 1 wherein the angle of the at least one side port is in the range of about 10 degrees to about 45 degrees.

10. The device of claim 1 wherein the angle of the at least one side port is in the range of about 15 degrees to about 45 degrees.

11. A device for venous valve repair comprising: (A) a catheter comprising: (i) a body having a proximal end and a distal end; (ii) a lumen, defined by the body of the catheter, that extends between the proximal end and the distal end of the catheter; (iii) at least one side port, defined by a distal end portion of the body of the catheter; and (iv) an expandable member; (B) a retractable and extendable member comprising: (i) a body having a proximal end and a distal end; (ii) a conduit, defined by the body of the retractable and extendable member, that extends between the proximal end and the distal end of the retractable and extendable member; (iii) at least one anchor positioned within the conduit; and (iv) an anchor deployment mechanism positioned within the conduit so as to cause deployment of the at least one anchor through the conduit and the at least one side port of the catheter when the anchor deployment mechanism is activated; wherein the retractable and extendable member is sized and configured to bend so as to form an angled portion thereof when the retractable and extendable member is in an extended position and to slide through the lumen of the catheter and extend through the at least one side port of the catheter; wherein when the retractable and extendable member is in the extended position, an angle in the range of greater than about 0 degrees and less than about 90 degrees is formed between (i) a transverse axis of the catheter that is orthogonal to a central longitudinal axis of the catheter, and (ii) a central axis of the angled portion of the retractable and extendable member.

12. The device according to claim 11, wherein the at least one side port is sized, configured and disposed so that it forms an angle in the range of greater than about 0 degrees and less than about 90 degrees, between a transverse axis of the catheter that is orthogonal to a central longitudinal axis of the catheter, and a central axis of the at least one side port, wherein all of the axes share a common intersection point.

13. The device according to claim 12, wherein the angle formed by the at least one side port is in the range of about 10 degrees to about 45 degrees.

14. The device according to claim 13, where in the angle formed by the at least one side port is in the range of about 15 degrees to about 45 degrees.

* * * * *